United States Patent [19]

Baker et al.

[11] Patent Number: 5,608,085

[45] Date of Patent: Mar. 4, 1997

[54] SYNTHESIS OF OPTICALLY ACTIVE CALANOLIDES A AND B AND ENANTIOMERS AND RELATED COMPOUNDS

[75] Inventors: David C. Baker; Prashant P. Deshtande; Shijia Yan; Frank Tagliaferri; Samuel F. Victory, all of Knoxville, Tenn.

[73] Assignee: The University of Tennessee Research Corporation, Knoxville, Tex.

[21] Appl. No.: 395,035

[22] Filed: Feb. 27, 1995

[51] Int. Cl.$^6$ ................................. C07D 311/78
[52] U.S. Cl. ........................... 549/277; 549/278
[58] Field of Search ........................... 549/277, 278

[56] References Cited

FOREIGN PATENT DOCUMENTS

WO9320082  10/1993  WIPO.
WO9414789   7/1994  WIPO.
WO9428000  12/1994  WIPO.

OTHER PUBLICATIONS

Application for Letters Patent No. 7/861,249, filed Mar. 31, 1992, Boyd, et al., Calanolide Antiviral Compounds, Compositions and Uses Thereof.

Taylor, P. B.; Culp, J. S., Debouck, C.; Johnson, R. K.; Patil, A. D.; Woolf, D. J.; Brooks, I.; Hertzberg, R. P. J. *J. Biol. Chem.* 1994, 269, 6325–6331.

Stout, G. H.; Stevens, K. L. *J. Org. Chem.* 1964, 29, 3604–3609.

Kashman, Y.; Gustafson, K. R.; Fuller, R. W.; Cardellina, J. H., II; McMahon, J. B.; Currens, M. J.; Buckhiet, R. W., Jr.; Hughes, S. H.; Cragg, G. M.; Boyd, M. R. *J. Med. Chem.* 1992, 35, 2735–2743.

Chenera, B.; West, M. L.; Finkelstein, J. A.; Dreyer, G. B. *J. Org. Chem.* 1993, 58, 5605–5606.

Fuller, R. W.; Bokesh, H. R.; Gustafson, K. R.; McKee, T. C.; Cardelina II, J. H.; McMahon, J. B.; Cragg, G. M.; Soejarto, D. D.; Boyd, M. R. *Bioorg. Med. Chem. Lett.* 1944 4, 1961–1964.

Newman, R. A.; Costa, M.; Cisneros, A. *J. Chromatogr. B* 1994, 658, 129–133.

Kawazu, K.; Ohigashi H.; Mitsui, T. *Tetrahedron Lett.* 1968, 2383–2385.

Kawazu, K.; Ohigashi H.; Takahashi, N.; Mitsui, T. *Bull. Chem Res. Kyoto Univ.* 1972, 50, 160–167; *Chem. Abstr.* 78:13744.

Patil, A. D.; Freyer, A. J.; Eggleston, D. S.; Haltiwagner, R. C.; Bean, M. F.; Taylor, P. B.; Caranfa, M. J.; Breen, A. L.; Bartus, H. R.; Johnson, R. K.; Hertzberg, R. P.; Westly, J. W. *J. Med. Chem.* 1993, 36, 4130–4138.

Stout, G. H.; Hickernell, G. K.; Sears, K. D. *J. Org. Chem.* 1968, 33., 4191–4200.

Polonsky, *J. Bull. Soc. Chim. Fr.* 1956, 914–922.

Polonsky, J.; Baskevitch, Z. *Bull. Soc. Chim. Fr.* 1958, 929–944.

Rao, A. V. R.; Gaitonde, A. S.; Prakash, K. R. C.; Rao, S. P. *Tetrahedron Lett.* 1994, 35, 6347–6350.

Application for Letters Patent No. 08/065,618, Calanolides and Related Antiviral Compounds, Compositions and Uses Thereof May 21, 1993.

*Primary Examiner*—C. Warren Ivy
*Assistant Examiner*—Raymond Covington
*Attorney, Agent, or Firm*—Weiser & Associates, P.C.

[57] ABSTRACT

A method of synthesis of the four optically active stereoisomers of calanolide A and B which produces the compounds in high yields and in a high degree of purity.

21 Claims, 7 Drawing Sheets

(+)-CALANOLIDE A $[\alpha]_D = +66°(c\,0.5,\ CHCl_3)$
$[\alpha]_D = +66°(c\,0.5,\ CHCl_3)^1$ (+)-CALANOLIDE B $[\alpha]_D = +44°(c\,1,\ CH_3COCH_3)$
$[\alpha]_D = +45°(c\,1.55,\ CH_3COCH_3)$
$[\alpha]_D = +10°(c\,1,\ CH_3COCH_3)^1$ (+)-CALANOLIDE A $[\alpha]_D = -66°(c\,0.5,\ CHCl_3)$

COSTATOLIDE $[\alpha]_D = -45°(c\,1,\ CH_3COCH_3)$
$[\alpha]_D = -50.4°(c\,1.55,\ CH_3COCH_3)^2$ CALANOLIDE A (1): $R_1$ = *n-propyl*, $R_2$ = OH, $R_3$ = H
CALANOLIDE B (2): $R_1$ = *n-propyl*, $R_2$ = H, $R_3$ = OH
INOPHYLLUM B (3): $R_1$ = *phenyl*, $R_1$ = OH, $R_3$ = H
INOPHYLLUM B (4): $R_1$ = *phenyl*, $R_1$ = H, $R_3$ = OH

CALANOLIDES:

CALANOLIDE A

CALANOLIDE B

INOPHYLLUMS:

INOPHYLLUM B

INOPHYLLUM P

INOPHYLLUM A

SYNTHESIS OF OPTICALLY ACTIVE CALANOLIDES A AND B AND ENANTIOMERS AND RELATED COMPOUNDS

BACKGROUND OF THE INVENTION

The dipyrano coumarins are a group of natural products from tropical plants of the genus Calophyllum, which are typified by coumarin, chroman, and chromene ring systems assembled about a phloroglucinol core. Calanolide A and B (costatolide) and inophyllums B and P are a group of dipyrano coumarins which have been identified in screening assays as potent inhibitors of human immunodeficiency virus-1 reverse transcriptase (HIV-1 RT).

The work in conjunction with this invention was supported, in part, by contracts N01-CM-17551 and -47038 from the Drug Synthesis and Chemistry Branch, Developmental Therapeutics Program of the National Cancer Institute.

FIELD OF THE INVENTION

The invention relates to a multistep synthesis of optically active calanolides A and B and their respective enantiomers which yields calanolides in high yields and in a degree of purity and free to a degree as not obtained with synthetic calanolides or inophyllums of their respective enantiomers and heretofore not reported in the literature. The calanolides are highly active against HIV-1 reverse transcriptase (RT).

PRIOR ART

Publications of interest relating to the subject matter of this invention include (a) Kashman, Y.; Gustafson, K. R.; Fuller, R. W.; Cardellina, J. H., II; McMahon, J. B.; Currens, M. J.; Buckhiet, R. W., Jr.; Hughes, S. H.; Cragg, G. M.; Boyd, M. R. *J. Med. Chem.* 1992, 35, 2735–2743. (b) Fuller, R. W.; Bokesh, H. R.; Gustafson, K. R.; McKee, T. C.; Cardelina II, J. H.; McMahon, J. B.; Cragg, G. M.; Soejarto, D. D.; Boyd, M. R. *Bioorg. Med. Chem. Lett.* 1994, 4, 1961–1964. (c) Newman, R. A.; Costa, M.; Cisneros, A. *J. Chromatogr. B* 1994, 658, 129–133.

(a) Kawazu, K.; Ohigashi H.; Mitsui, T. *Tetrahedron Lett.* 1968, 2383–2385. (b) Kawazu, K.; Ohigashi H.; Takahashi, N.; Mitsui, T. *Bull. Chem. Res. Kyoto Univ.* 1972, 50, 160–167; *Chem. Abstr.* 78:13744.

Patil, A. D.; Freyer, A. J.; Eggleston, D. S.; Haltiwagner, R. C.; Bean, M. F.; Taylor, P. B.; Caranfa, M. J.; Breen, A. L.; Bartus, H. R.; Johnson, R. K.; Hertzberg, R. P.; Westly, J. W. *J. Med. Chem.* 1993, 36, 4130–4138.

Taylor, P. B.; Culp, J. S.; Debouck, C.; Johnson, R. K.; Patil, A. D.; Woolf, D. J.; Brooks, I.; Hertzberg, R. P. *J. Biol. Chem.* 1994, 269, 6325–6331.

Chenera, B.; West, M. L.; Finkelstein, J. A.; Dreyer, G. B. *J. Org. Chem.* 1993, 58, 5605–5606.

(a) Stout, G. H.; Stevens, K. L. *J. Org. Chem.* 1964, 29, 3604–3609; (b) Stout, G. H.; Hickernell, G. K.; Sears, K. D. *J. Org. Chem.* 1968, 33, 4191–4200.

Polonsky, J. *Bull. Soc. Chim. Fr.* 1956, 914–922; Polonsky, J.; Baskevitch, Z. *Bull. Soc. Chim. Fr.* 1958, 929–944.

Rao, A. V. R.; Gaitonde, A. S.; Prakash, K. R. C.; Rao, S. P. *Tetrahedron Lett.* 1994, 35, 6347–6350.

PCT International Publication WO 93/2008, published Oct. 14, 1993, Boyd, et al., Calanolide Antiviral Compounds, Compositions and Uses Thereof.

PCT International Publication WO 94/14789, published Jul. 7, 1994, Patil, et al., Coumarin Derivatives as Retroviral Inhibitors.

PCT International Publication WO 94/28000, published Dec. 8, 1994, Boyd, et al., Calanolide and Related Antiviral Compounds, Compositions, and Uses Thereof.

All the references are incorporated herein by reference, in particular the three PCT publications.

The compounds synthesized by the method of the invention are characterized by a ring system built around a phloroglucinol core, with common structural features that include a chromene ring, a coumarin ring, and most essential for their optical activity and their biological activity, a 2,3-dimethylchroman-4-ol (3,4-dihydro-2H-benzo[b]pyran system) bearing methyl groups at C-2 and C-3 in a trans relationship and a hydroxy group at C-4 (chroman numbering). A number of syntheses of racemic calanolides[5–7] and other calophyllum coumarins[8] have been published. One multistep synthesis of optically active 2,3-methylchroman-4-ones and subsequent diastereoselective reduction to the chroman-4-ols has been recently reported.[9]

SUMMARY OF THE INVENTION

The invention provides a novel synthesis of the four optically active stereoisomers of both calanolides A and B using a process that generates all three contiguous chiral centers in a most expeditious manner. Until now the synthesis of optically active calanolides has not been reported.

The method of the invention broadly involves a stereoselective synthesis of the chiral 2,3-dimethylchroman-4-ol ring from a silyl-protected salicylaldehyde.[10] The chiral centers at C-3 and C-4 (chroman numbering) were introduced using (Z)-crotyldiisopinocampheylborane-sodium perborate oxidation, and then a mercury-assisted cyclization of the resulting orthoalkenyl phenol was implemented to give the required trans, trans-Me-Me-OH substituted chroman (benzo[b]pyran ring).

The synthesis of the optically active calanolides A and B involves installing two of the three chiral centers with the appropriate diisopinocampheylborane (the (−)-(E)-crotyl- or the (+)-(E)-crotyl), generating the pyran ring by $Hg(OAc)_2$-mediated ring closure to give calanolide B. Calanolide A is synthesized from calanolide B by a modified Mitsunobu reaction on calanolide B using $Me_3P/DEAD/ClCH_2CO_2H$. Both sets of enantiomers were made using the (+)- and (−)-boranes.

The four optically active calanolides are obtained in high yields and in a degree of purity heretofore not reported in the literature. The calanolides of the invention are solid crystalline products which distinguish themselves from those published in the literature by their respective melting points, their respective optical rotations and other analytical data. The biological and anti-HIV-1-RT activity of two of the biologically most active calanolides (+)-calanolide A and (−)-calanolide B appears to be different, if not superior to the corresponding activity of the known and reported calanolides. This is presumably because the biologically active calanolides obtained by the synthesis of the invention are virtually, i.e., more than 95%, generally 98% pure and free of the corresponding enantiomers.

In the process of the invention there are synthesized novel heterocyclic chromene-6-, chromene-8-, and chromene-2- compounds which are useful in the synthesis of the other ring compounds of the invention, in other reactions as starting molecules, or as intermediates, and these compounds are expected to have biological activity of interest.

The synthesis of the invention is applicable to the class of structurally analogous compounds which includes the calanolides, the inophyllums, the costatolides, the cordatolides and others, generically referred to in the literature and herein as dipyrano coumarins.

The calanolides[1] (+)-calanolide A and (−)-calanolide B and their analogues, particularly the inophyllums[2-3] are potent non-nucleoside inhibitors of HIV-1 reverse transcriptase.[4] It has been reported that these dipyrano coumarins differ from nucleoside inhibitors in the distinct pattern of amino acid changes required to confer resistance, indicating that the RT binding sites for these compounds are overlapping but not identical. It is believed that these coumarins could be less prone to elicit viral resistance.

The respective optical rotations found for the calanolides synthesized by the method of the invention and below that data, for these calanolides as reported in the literature, are shown.

Figure 1:
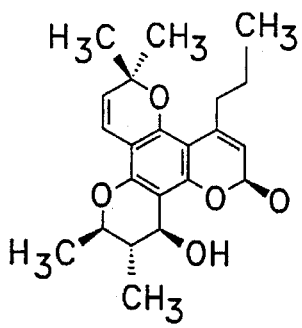
FIG. 1 illustrates the structure of the Calanolides A and B and their enantiomers.
Figure 1:
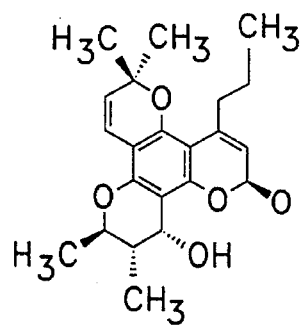
Figure 1:
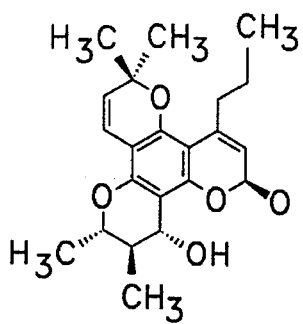
Figure 1:
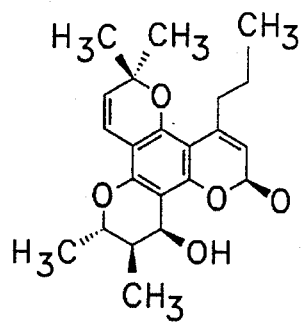
Figure 2:
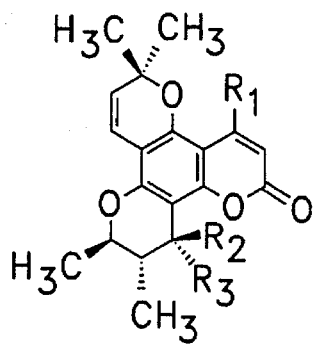
FIG. 2 illustrates in a generic formula the structure of Calanolide A(1), Calanolide B(2), Inophyllum B(3) and Inophyllum P(4).
Figure 3:
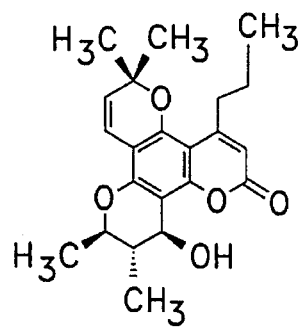
Figure 3:
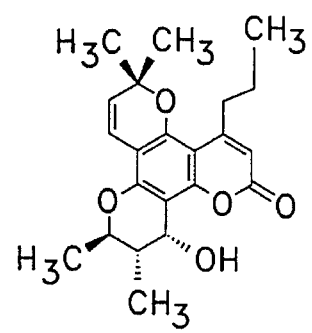
Figure 3:
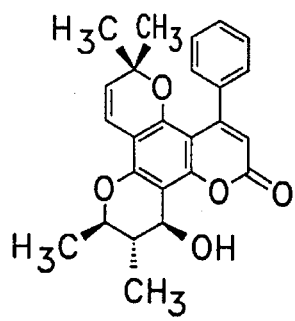
Figure 3:
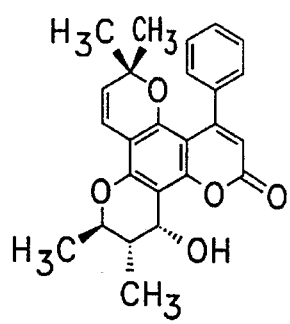
Figure 3:
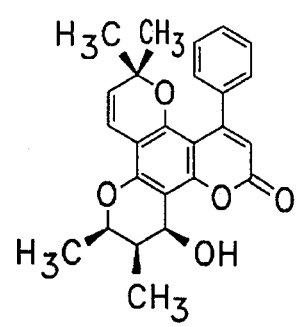

FIG. 3 illustrates the structure of Calanolide A and Calanolide B, Inophyllum B, Inophyllum P and Inophyllum A.

Figure 4:
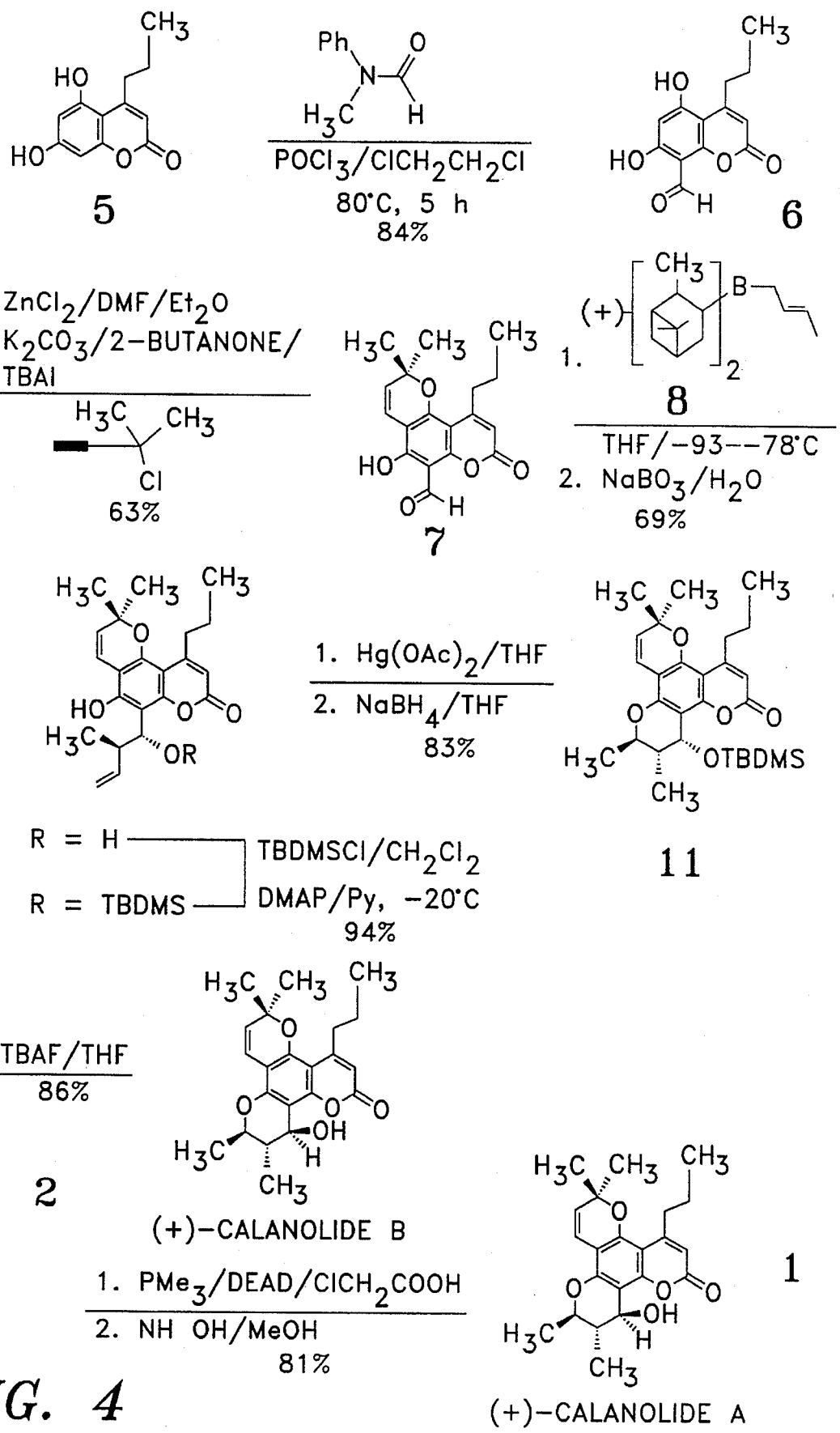

FIG. 4 illustrates Scheme 1 of the synthesis of (+)-Calanolide B and Calanolide A by the synthesis of the invention.

Figure 5:
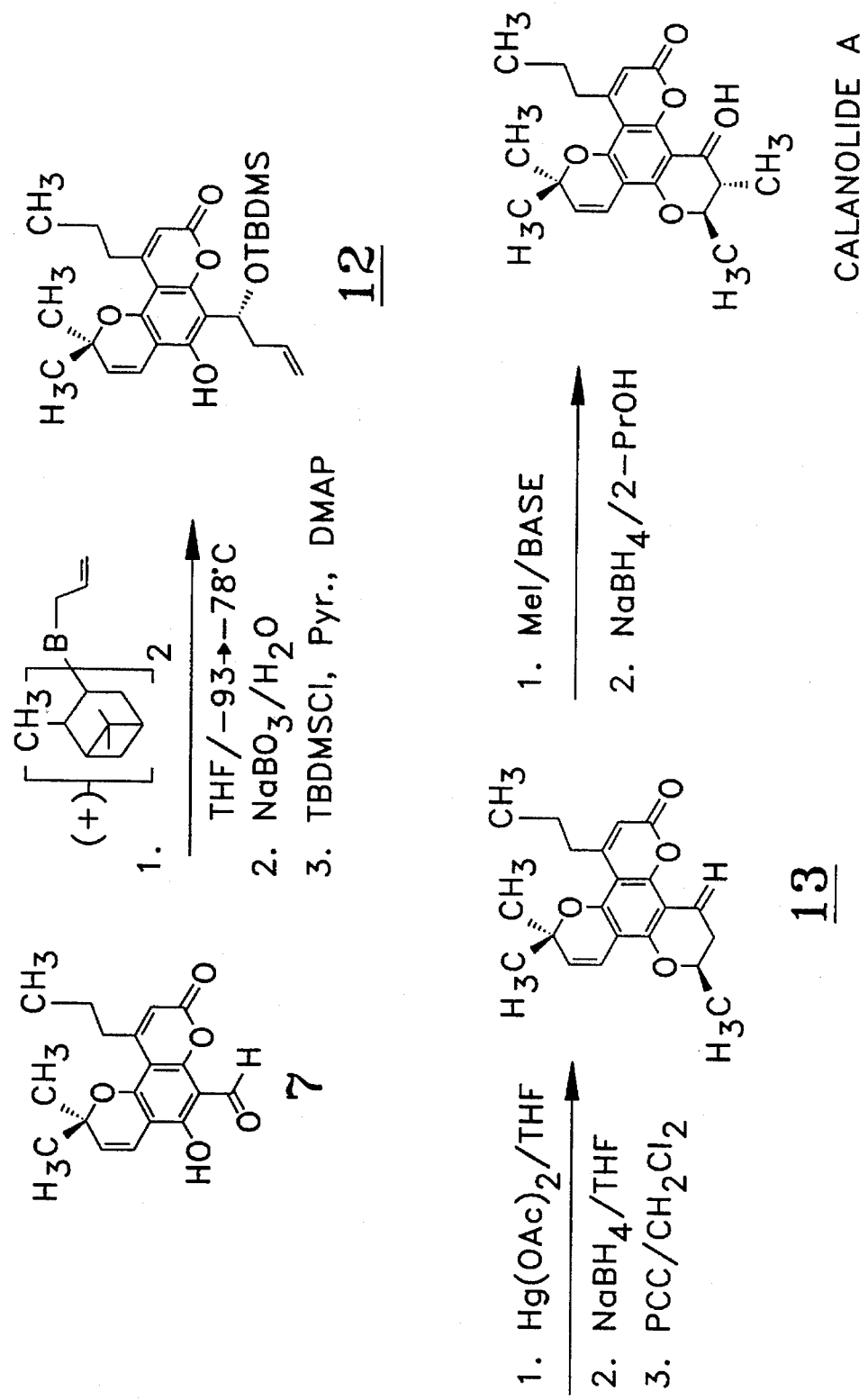

FIG. 5 illustrates an alternative Scheme 2 of the synthesis of the invention.

Figure 6:
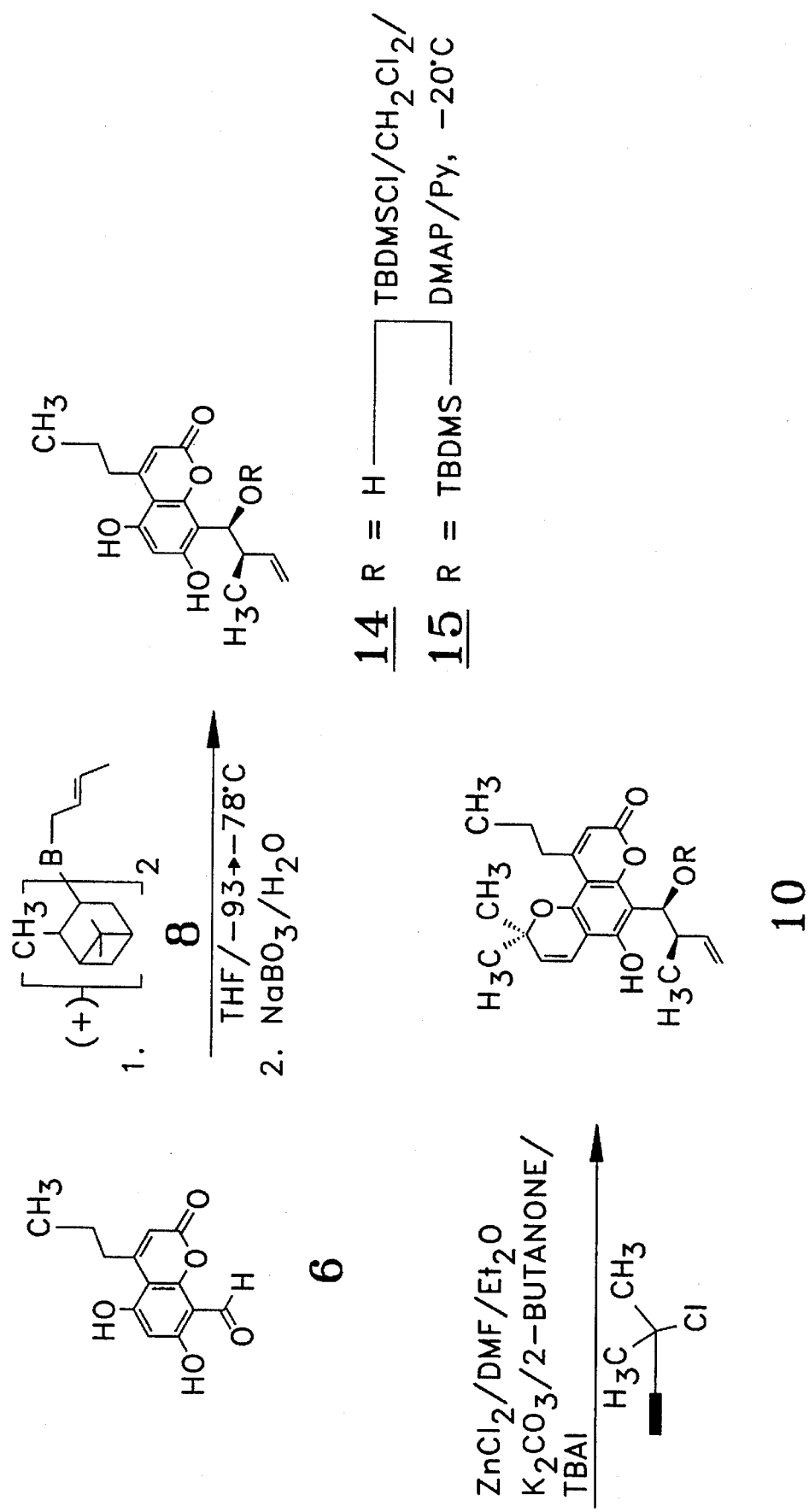

FIG. 6 illustrates another variant, Scheme 3 of the invention.

Figure 7:
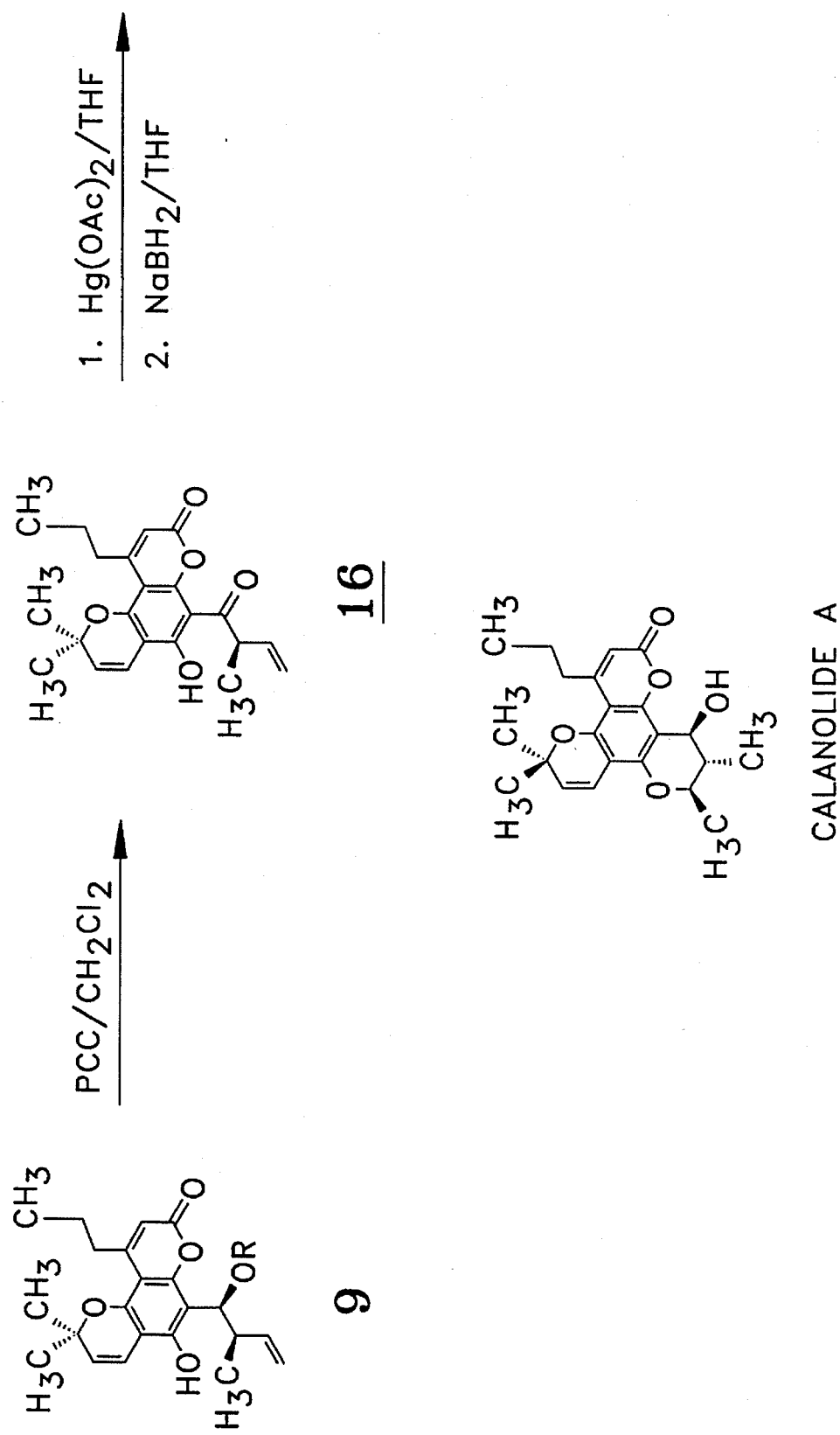

FIG. 7 illustrates another variant, Scheme 4 of the synthesis of the invention.

In the text and in the FIGS. the designation of "a" after a compound number indicates the (−)-enantiomer of the structures described in the text and depicted in the Figures.

NOMENCLATURE AND KEY TO COMPOUNDS

In the description of the invention and in the Figures, the calanolides and other compounds will be referred to by numerals or other abbreviations as appropriate.

DESCRIPTION OF THE BEST MODE

The best mode of carrying out the synthesis of the calanolides is depicted in Scheme 1 (FIG. 4).

In the synthesis of the optically active calanolides A and B, their enantiomers and the intermediates we used as starting compound the known coumarin lactone (5) which may be prepared from phloroglucinol as described by Chenera et al.,[5]. To introduce an aldehyde function at the C-8 position, we reacted the coumarin lactone (5) with N-methylformanilide in the presence of POCl$_3$ in dichloroethane at 70°–75° C. We obtained the formylated coumarin lactone (6) in 84% yield, a crystallized product with a melting point of 236°–237° C. This is a new compound. The regiochemistry of the formylation was confirmed by NOE studies.

To introduce regioselectively the essential dimethylchromene ring at the phenolic hydroxy group C-6, we reacted the formylated coumarin (6) with 3-chloro-3-methyl-1-butyne, potassium carbonate, Bu$_4$NI in DMF and 2-butenone, heated the reaction mixture to 60° C., added anhydrous zinc chloride in diethyl ether at 60° C., heated for 1hr, added additional anhydrous zinc chloride and maintained the temperature at 60° C. for several hours (to a total of 36 hrs).

The chromene-6-carbaldehyde (7) was obtained in 63% yield as a yellow solid of melting point 116°–117° C. This chromene is a new compound.

To construct the enantiomerically pure trans-2,3-dimethyl chroman-4-ol, we proceeded to prepare threo-β-methyl homoallylic alcohol (9) using hydroboration-oxidation with (+)-(E)-crotyldiisopinocampheylborane (8) and sodium perborate. The organoborane reagent was prepared as described by Brown and Bhat[15]. The organoborane was reacted with the chromene-6-carbaldehyde (7) at the low temperature of −93° C. to obtain threo-β-methyl homoallylic alcohol (9) in 66% yield, as a syrup of an optical rotation of $[\alpha]_D^{20}$+78° (c 1.0, acetone). This is a new substance.

Sodium perborate was used during the work up to oxidize the boron-carbon bond. No racemation[12] of the C-4 (chroman numbering) chiral center was observed by either TLC or $^1$H NMR spectroscopy of the product.

The monosilylation of (9) was performed with TBDMSCl-pyridine-DMAP in CH$_2$Cl$_2$ at −20° C., yielding quantitatively the monosilylated orthoalkenyl phenol (10) as a syrup in 95% yield; optical rotation $[\alpha]_D^{20}$+26.0° (c 3.8, acetone) This is also a new substance.

It is possible that the phenolic hydroxy group is less accessible than the homoallylic alcohol due to steric interaction with the alkene proton at C-4, leading to preponderant monosilylation.

Mercury-assisted cyclization of the orthoalkenyl phenol[18] (10) was carried out with mercury(II) acetate[19] in THF, and the intermediate organomercurial was reduced with excess sodium borohydride to obtain silyl-protected (+)-calanolide B (11) in 83% yield, $[\alpha]_D^{20}$−41° (c 1.0, acetone). Deprotection of the silyl group with tetrabutylammonium fluoride gave (+)-calanolide B[11] in 86% yield, mp 176° C., $[\alpha]_D^{20}$+44.0° (c 1.0, acetone). The $^1$H and $^{13}$C NMR spectra were identical with those of the natural product. [1a]

The optical rotation and melting point are different from the data reported in the literature indicating that this enantiomer is purer. This was confirmed by determination of the enantiomeric ratio, which was determined by $^1$H, $^{13}$C and $^{19}$F NMR analysis of the α-methyl-α-(trifluoromethyl)phenylacetate (i.e., the Mosher ester)[20] of the synthetic (+)-calanolide B (2) and was found to be >98%.

For the synthesis of the inophyllums by the method of the invention, the phenyl-substituted reactant is used instead of the corresponding alkyl (e.g., propyl)-substituted reactant. The corresponding inophyllums are obtained.

(+)-Calanolide B which has been reported as a natural product appears to have an optical rotation of $[\alpha]_D^{20}$+10° (c 1.0, acetone)[1]

The conversion of (+)-calanolide B (2) into (+)-calanolide A (1) was efficiently carried out with a modified[21] Mitsunobu reaction. [22] Compound (2) was reacted with PMe$_3$, diethyl azodicarboxylate (DEAD), and chloroacetic acid, and the resulting ester was saponified with ammonium hydroxide in MeOH, giving after purification by silica gel chromatography, (+)-calanolide A (1) in 81% yield (mp 45°–48° C.), $[\alpha]_D^{20}$+66° (c 0.5, CHCl$_3$), {lit.[1a] $[\alpha]_D$+60° (c 0.5 CHCl$_3$)}. Again, the $^1$H and $^{13}$C NMR spectra were identical with those reported for the natural product.[1a] This isomer is purer than that reported in the literature which has a $[\alpha]_D$+60° (c 0.5 CHCl$_3$)[1]. The enantiomeric ratio was determined to be 98:2.

The entire process in Scheme 1 was repeated using (–)-(E)-crotyldiisopinocampheylborane (8a) in order to provide the (–)-calanolide B [costatolide (2a)] {$[\alpha]_D^{20}$–45° (c 1.0, acetone), (lit.[7a] $[\alpha]_D^{25}$–50.4° (c 1.55, acetone)}. The enantiomeric ratio was determined to be 98:2.

For the synthesis of (–)-calanolide A (1a), (–)-calanolide B was treated under the modified Mitsunobu conditions to give compound (1a) as a white solid in 81% yield mp 44°–47° C. $[\alpha]_D^{20}$–66° (c 0.5, CHCl$_3$). The enantiomeric ratio was determined to be 98:2.

This compound has not been reported in literature.

ALTERNATIVE EMBODIMENTS

The synthesis of the invention lends itself to alternatives and a different sequence of steps or route to the desired products.

To synthesize the formylated lactone (6) from the coumarin lactone (5) there may be used other formamides like N-methylformanilide or other N,N-dialkyl-, N,N-arylalkyl- or N,N-diarylformamides, especially N,N-dimethylformamide, in the presence of POCl$_3$ or other related chalcogen-metal halides, or phosgene (COCl$_2$), in 1,2-dichloroethane or other aprotic nonpolar solvent, including chlorinated hydrocarbons. "Alkyl" is generally lower alkyl of 1 to 4 carbon atoms, preferably methyl. "Aryl" is generally phenyl, or lower alkyl substituted phenyl.

The temperature of reaction is in the range of 40°–100° C., preferably in 1,2-dichloroethane at about 80° C. under conditions of a typical Vilsmeier reaction[13]. Other methods of aromatic ring formylation, e.g., the Gatterman-Koch reaction [Crounse, N. N. Org. Reactions 1949, 5, 290–300] or the Gatterman aldehyde reaction [Truce, W. E. Org. Reactions 1957, 9, 38–72], or improved versions thereof, may be used.

For the synthesis of the chromene-6-carbaldehyde (7) there may be used any other reagents: propargylic halides like aryl propargyl ethers to form ortho-alkenyl phenol intermediates, which cyclize to chromenes or any 3-halo-3-methyl-1-butyne, an alkali metal or alkaline earth metal base, or organic amine, K$_2$CO$_3$ being preferred, with or without addition of an iodide salt, the preferred conditions being with a tetraalkyl- or tetraarylammonium iodide, especially (Bu)$_4$NI, in an aprotic, polar solvent or solvent mixture, N,N-dimethylformamide-2-butenone mixtures being preferred. Instead of Bu$_4$NI, Bu$_4$KI may be considered. Other solvents include various dialkyl ketones, dialkyl- or mixed aryl-alkylformamides, dimethyl sulfoxide, sulfolane, hexamethylphosphoric triamide or tetramethylurea. Other Lewis acids, e.g., SnCl$_4$, TiCl$_4$, or AlCl$_3$, may be substituted for ZnCl$_2$. Temperatures for ring formation may vary from 0°–150° C., with ranges from 50° to 120° being acceptable, 70° to 60° C. being preferred. Times may vary from 1–48 h, with 12 h being preferred.

An alternative procedure, or modifications as published by Godfrey and co-workers [Godfrey, J. D., Jr.; Mueller, R. H.; Sedergran, T. C.; Soundarajan, N.; and Colandrea, V. J. Tetrahedron Lett. 1994, 35, 6405–6408] may be used. Under these conditions the aromatic compound is treated at 0° C. with a 2-methyl-but-3-yne-2-ol, or one of its ester derivatives, with Cu(I) or Cu(II) salts in an aprotic solvent to obtain the propargylic ether, which is then ring-closed with a suitable Lewis acid as described herein above.

In order to synthesize the enantiomerically pure β-homoallylic alcohol (9), there may be used any appropriate organoborane optically active reagent like any crotyl-substituted organometallic reagent (type M-crotyl) bearing a suitable optically active ligand, where M=B, Sn, Al, Si, Ti or other metal or metalloid. The optically active ligands may be of any suitable, asymmetric organic moiety that might include, but is not restricted to, the following: monoisocampheylborane,[24] limonylborane,[25] 2-, and 4-dicaranylboranes,[26] myrtanylborane,[27] or dilongifolylborane,[28] disclosed in the respective references identified below.

It is noted that the enantiomeric series leading to the (+)-calanolides or to the (–)-calanolides, as well as the enantiomeric purity thereof, is largely determined by the choice of optically active ligand. By appropriate selection from the optically active ligands disclosed herein and others available in the literature, one skilled in the art will readily select the appropriate ligand to yield the desired calanolide or inophyllum.

The temperature of reaction may vary between –20° and –110° C., with the range of –93° C. up to –78° C. being preferred. Times may vary from 0.1 h to 24 h; however, a period of 0.5 h at –93° C., followed by stirring at –78° C. is preferred. Oxidative workup may be carried out with H$_2$O$_2$ and alkali metal or alkaline earth metal base, but sodium perborate[17] is preferred.

As an alternate to Scheme 1, Scheme 2 (FIG. 5) may be used from the chromene-6-carbaldehyde (7) by adapting the method of Rama Rao and co-workers [Rama Rao, A. V.; Gaitonde, A. S.; Prakash, K. R. C.; Prahlada Rao, S. Tetrahedron Lett. 1994, 35, 6347–6350]. Thus reaction of 7 with allyl-M (where M=B, Al, Sn, Ti or related species), followed by silylation with TBDMSCL, gives protected β-homoallylic alcohol (12). Ring closure as described above (oxymercuration-demercuration), deprotection and oxidation, gives the ketone. Oxidants include pyridinium chlorochromate, pyridinium dichromate or other chromium-based reagent, or a dimethyl sulfoxide-based reagent, or a suitable catalyst and oxygen. Subsequent α-alkylation with MeI, (MeO)$_2$SO$_2$ or related reagent in suitable base, will give the resultant 10,11-dimethylpyranone. Reduction of the pyranone intermediate with NaBH$_4$, as described above, or with a related alkali or alkaline earth metal borohydride or other selective metal hydride reducing agent, gives the 12-OH compound. Especially selective are a number of oxidoreductases, either crude, purified, or immobilized, that are available from yeast or other microbial sources that are known to selectively reduce such ketones [Roberts, S. M., Preparative Biotransformations, Wiley: New York, 1993, chapter 2].

An alternative route of synthesis to that depicted in Scheme 1 may be followed as depicted in Scheme 3 (FIG. 6). Instead of following the order of the steps as shown in Scheme 1 from compounds (6) to (10), compound 6 may be reacted directly with the organometallic reagent (8), giving product (14) as shown in Scheme 3. Silylation then gives (15) on which chromene ring formation as previously described furnished (10). Essentially the same conditions are employed as for steps 6→7→9→10. However, the order of 6→7→9→10 as shown in Scheme 1, is the preferred sequence of steps.

Alternative reagents for the silylation of (9) include Me$_3$SiX, t-BuPh$_2$SiX, or other trialkyl-, mixed aryl-alkyl- or triarylsilyl halide with suitable base in a dry, aprotic solvent.

X may be a halogen or other suitable leaving group, e.g., sulfonic acid ester, perchlorate, and the like. The TBDMSCl (t-BuMe$_2$SiCl) reagent is, however, preferred. Reaction temperatures may range from −50° to +50° C.; however, −10° to −30° C. may be satisfactory, about −20° C. being preferred.

While bulky silicon-based protective groups for the 1'-OH functional group of (9) are preferred, any alkyl, aryl, or acyl derivative capable of forming a suitable protective ether or ester derivative for the 1'-OH group may be used.

Alternatives to the mercury-assisted cyclization of the orthoalkenylphenol (10) may be used as any electrophilic process, known to ring-close acyclic alkenes with phenolic compounds to form O-heterocycles, may be employed. Reagents include Lewis acids of various types, e.g., halogens, especially iodine; N-haloimides, especially, N-bromosuccinimide; alkyl- and arylselenium halides of the type RSeX; and sulfur halide reagents of the type RSX.

Alternatively, ring closure could also be effected on the keto compound (16) obtained from compound (9) as shown in Scheme 4 (FIG. 7). Thus oxidation using pyridinium chlorochromate, pyridinium dichromate, or related chromium-based reagents, dimethyl Sulfoxide-based reagents, catalytic oxidations with oxygen, or any of a number of reagents known to oxidize secondary alcohols to ketones, gives the corresponding ketone (16). Ring closure may be effected by any of the procedures outlined for the conversion of compounds (10) to (11). The 12-OH functional group may then be generated using any number of mild, selective reducing agents, e.g., NaBH$_4$ or any alkali metal, alkaline earth metal, or tetraalkyl- or mixed akyl-arylammonium borohydride or related species. Exceptionally mild, selective reagents include various oxidoreductases from various yeasts and bacterial sources that are capable of converting such ketones to secondary alcohols. [*Preparative Biotransformations* ref. in section above].

For the reduction of the intermediate organomercurial in the mercury mediated cyclization of (10) alternatives to NaBH$_4$ are available which include any alkali metal or alkaline earth metal borohydride or tetraalkyl- or mixed alkyl-arylammonium borohydride or triakyloxyborohydrides in suitable protic or aprotic solvent. Other appropriate metal hydrides, e.g., organoaluminum hydrides, or hydrides of alkali or alkaline earth metals, may be used.

Desilylation of the silyl-protected (+)-calanolide B (11) may be performed by other reagents including any tetraalkyl-, tetraaryl- or mixed alkyl-arylammonium fluoride, pyridinium fluoride, HF-acetonitrile or solutions of HF salts in aprotic media, or the common mineral acids in aprotic or protic media.

To convert (+)-calanolide B to its isomer, (+)-calanolide A, a modification of the Mitsunobu reaction[21] was used which involved the use of ClCH$_2$CO$_2$H instead of the usual RCO$_2$H reagents, where R=alkyl or aryl. The α-chloroacetate intermediate is exceptionally facile of cleavage under mildly basic conditions. Acidic ArOH compounds may also be used. A further modification to the Mitsunobu reaction in accordance with the invention is the use of Me$_3$P instead of the usual Ph$_3$P reagent. Advantages of Me$_3$P over the latter apparently lie in its smaller steric bulk that facilitates reaction with the 12-OH compound and the fact that unreacted reagent is easily removed. Alternatives to Me$_3$P include any trialkyl-, triaryl- or mixed alkyl-arylphosphine reagents as taught in the seminal work of O. Mitsunobu.[22] Alternatives to diethylazodicarboxylate include any dialkyl-, diaryl-, or mixed alky-arylazodicarboxylate reagent. Temperatures may range from −100° C. to 40° C. although the range of −78° C. to −30° C. is the preferred range.

Saponification of the resulting carboxylic acid ester intermediate is preferentially effected with ammonium hydroxide-methanol mixtures at −30° C. to +40° C., although a range of −30° C. to 0° C. is preferred. Any trialkyl-, triaryl- or mixed alkyl-arylammonium base or other alkali or alkaline earth metal hydroxide may be used, although NH$_4$OH in MeOH is the preferred reagent. Alternatively NH$_4$OH in acetonitrile or other aprotic solvent can be used.

To prepare the (−)-calanolide B (costatolide)2a, the alternate Schemes 2, 3, and 4 may be followed.

Whenever a temperature range is provided, it will be understood that operating outside of the range is likely to give less than optimum results.

EXAMPLES

The following examples are only illustrative of the invention and are not to be construed as limiting its scope.

General Methods

All reactions were monitored by thin-layer chromatography (TLC). Adsorption chromatography was carried out using E. Merck silica gel products: (a) TLC on 0.2-mm aluminum-backed plates, (b) column chromatography using 230–400 mesh silica gel. Visualization of the TLC plates was by 254-nm UV light and by spray-heat development using an p-anisaldehyde-sulfuric acid reagent.[23] The solvent system for column chromatography was A, 9:1 hexanes-ethyl acetate; B, 49:1 hexanes-ethyl acetate. Anhydrous solvents were prepared as follows: methylene dichloride, pyridine and triethylamine were distilled from calcium hydride. Diethyl ether was distilled over lithium aluminum hydride. THF was refluxed with sodium-benzophenone ketyl and distilled. N,N-Dimethylformamide was distilled over calcium hydride under reduced pressure. All reactions were carried out under a nitrogen atmosphere unless otherwise indicated. Solvents were evaporated at aspirator vacuum at about 40° C., unless otherwise indicated. Melting points were determined using a Thomas-Hoover "Unimelt" capillary melting point apparatus equipped with a Cole-Parmer model 8520-50 Digi-Sense digital thermocouple combination that was calibrated with known standards. Elemental analyses were furnished by Atlantic Microlab, Inc. of Atlanta, Ga. $^1$H and $^{13}$C NMR spectra were determined at 250 MHz and 62.5 Hz, respectively, as ca. 0.1% solutions in chloroform-d using a Bruker AM 250 instrument. $^1$H NMR chemical shifts are reported as δ (ppm) downfield from an internal standard of tetramethylsilane (TMS); multiplicities are first-order values in Hz: s, singlet; d, doublet; t, triplet; dd, doublet of doublets; m, multiplet. The exchangeable protons of hydroxy groups were determined by deuterium exchange using deuterium oxide. $^{13}$C NMR chemical shifts are reported as δ (ppm) relative to CDCl$_3$ (77.00 ppm) as standard. Optical rotations were measured with a Perkin-Elmer Model 243 automatic polarimeter for solutions in a 0.1-dm cell at the indicated temperature. The mass spectral analysis was obtained on a VG-ZAB instrument at the University of Tennessee.

PREPARATION OF CALANOLIDES AND THE INTERMEDIATES 5,7-Dihydroxy-2-oxo-4-propyl-2H-chromene-8-carbaldehyde (6)

To a solution of 5[5] (20.0 g, 90.8 mmol) in ClCH$_2$CH$_2$Cl (90 mL), was added N-methylformanilide (24.55 g, 181.6 mmol) and POCl$_3$ (15.31 g, 99.89 mmol). The reaction mixture was stirred at 75° C. for 4 h and then allowed to cool to room temperature. The solution was then neutralized by the dropwise addition of saturated aqueous NaOAc. The solid that formed was filtered, dried and recrystallized from MeOH to give 6 (19 g, 84%) as a white solid: mp 236°–237° C.; $^1$H NMR (DMSO): δ 0.957 (t, 3H, J=7.3 Hz, —CH$_2$CH$_3$), 1.57 (m, 2H, —CH$_2$—CH$_3$), 2.83 (t, 2H, J=7.5 Hz, —CH$_2$CH$_2$CH$_3$), 6.01 (s, 1H, H-3), 6.21 (s, 1H, H-6), 10.13 (s, 1H, —CHO), 11.90 (bs, 1H, —OH), 12.20 (s, 1H, —OH); $^{13}$C NMR (DMSO) δ 13.70, 22.30, 37.22, 98.86, 101.92, 103.24, 109.79, 158.23, 158.74, 164.99, 190.43. Anal. Calcd for C$_{13}$H$_{12}$O$_5$: C, 62.90; H, 4.87. Found: C, 62.94; H, 4.79.

For preparation of the corresponding inophyllum intermediate, 5,7-dihydro-4-phenylcoumarin was substituted for 5,7-dihydro-4-(n-propyl)coumarin.

5-Hydroxy-2,2-dimethyl-8-oxo-10-propyl-2H,8H-pyrano [2,3-f]chromene-6-carbaldehyde (7)

To a solution of 6 (5.60 g, 22.5 mmol) in 2-butanone (125 mL) and dry DMF (10 mL) was added potassium carbonate (13.2 g, 95.5 mmol), tetrabutylammonium iodide (12.2 g, 33.0 mmol) and 3-chloro-3-methyl-1-butyne (11.2 g, 109 mmol). The reaction mixture was heated at 60° C. for 1 h, at which time anhydrous ZnCl$_2$ (16 mL, 1 M solution in ether) was added. The reaction mixture was then heated at 60° C. for 12 h. Additional anhydrous ZnCl$_2$ (8 mL, 1M solution in ether) was added, and the reaction mixture was kept at 60° C. for another 24 hr. The reaction mixture was cooled, quenched with saturated aqueous NH$_4$Cl (150 mL), and extracted with EtOAc (3×100 mL). The combined organic layers were then washed with brine (1×50 mL), dried (MgSO$_4$), concentrated and submitted to silica gel chromatography (solvent B) to obtain 7 (4.46 g, 63%) as a yellow solid: mp 116°–117° C.; $^1$H NMR (3:2 CDCl$_3$-CD$_3$OD): δ 1.08 (t, J=7.3 Hz, 3H, —CH$_2$CH$_3$), 1.57 (s, 6H, —C(CH$_3$)$_2$), 1.68 (m, 2H, —CH$_2$CH$_3$), 2.90 (t, 2H, J=7.7 Hz, —CH$_2$CH$_2$CH$_3$), 5.67 (d, 1H, J=10.0 Hz, H-3), 6.02 (s, 1H, H-9), 6.62 (d, 1H, J=10.0 Hz, H-4), 10.29 (s, 1H, —CHO); $^{13}$C NMR (3:2 CDCl$_3$-CD$_3$OD): δ 12.79, 22.44, 27.15, 37.76, 79.87, 102.02, 103.08, 104.74, 110.18, 113.91, 126.31, 157.30, 157.54, 158.09, 158.91, 160.21, 192.12. Anal. Calcd for C$_{18}$H$_{18}$O$_5$: C, 68.78; H, 5.77. Found C, 68.77; H, 5.79.

For preparation of the corresponding inophyllum intermediate, the 4-phenyl analogue was substituted for 5,7-dihydroxy-2-oxo-4-propyl-2H-chromene-8-carbaldehyde.

(+)-5-Hydroxy-6-[(1R,2R)-1-hydroxy-2-methylbut-3-enyl]-2,2-dimethyl-10-propyl-2H-pyrano[2,3-f]chromene-8-one (9)

The organoborane reagent 8 was prepared according to the procedure of Brown and Bhat[5]. To a stirred mixture of t-BuOK (1.15 g, 10.2 mmol) and trans-2-butene (4.0 mL, 44 mmol) in THF (8 mL) maintained at −78° C., was added BuLi (4.10 mL, 10.2 mmol, 2.5 M in hexanes). The mixture was then kept at −60° C. for 10 min and cooled to −93° C., at which time (+)-(E)-crotyldiisopinocampheylborane (8) (3.89 g, 12.3 mmol) in diethyl ether (14 mL) was added dropwise over a period of 18 min. The reaction mixture was stirred at −93° C. for 30 min, and boron trifluoride etherate (1.63 mL, 13.3 mmol) was then added dropwise over 3 min, followed by compound 7 (2.02 g, 6.43 mmol) in 1:1 Et$_2$O-THF (20 mL) over a period of 12 min. The mixture was stirred at −93° C. for 30 min, then at −78° C. for 5 h. After this time sodium perborate[17] (12.3 g, 79.9 mmol) and water (11 mL) were added, and the mixture was stirred for 10 h at room temperature. Brine (30 mL) was added, and the organic layer was separated. The aqueous layer was extracted with EtOAc (2×40 mL), and the combined organic layers were dried (MgSO$_4$), concentrated, and submitted to silica gel chromatography (solvent A) to obtain 9 (1.58 g, 66%) as a syrup: [α]$_D^{20}$+78° (c 1.0, acetone); $^1$H NMR (CDCl$_3$): δ 0.93 (t, 3H, J=7.40 Hz, —CH$_2$CH$_3$), 0.96 (d, 3H, J=6.80 Hz, —CHCH$_3$), 1.37, 1.43 (2s, 6H, —C(CH$_3$)$_2$), 1.51 (m, 2H, —CH$_2$CH$_3$), 2.56 (m, 1H, —CHCH$_3$), 2.62–2.88 (m, 2H, —CH$_2$CH$_2$CH$_3$), 4.57 (bs, 1H, —OH), 4.92–5.10 (m, 2H, —CH=CH$_2$), 5.29 (d, 1H, J=7.0 Hz, —CHOH), 5.46 (d, 1H, J=10.0 Hz, H-3), 5.64 (s, 1H, H-9), 5.77–5.96 (m, 1H, —CH=CH$_2$), 6.60 (d, 1H, J=10.0 Hz, H-4), 9.84 (s, 1H, Ar—OH); $^{13}$C NMR (CDCl$_3$): δ 13.95, 16.38, 22.96, 27.35, 28.05, 38.48, 44.05, 72.60, 77.54, 102.71, 106.35, 107.09, 109.05, 116.27, 116.52, 126.66, 139.60, 151.00, 151.66, 156.03, 159.41, 161.67. Anal. Calcd for C$_{22}$H$_{26}$O$_5$: C, 71.33; H, 7.07. Found C, 70.46; H, 7.02. MS (negative-ion FAB): m/z 369 (M−1)$^-$, 315.

For preparation of the corresponding inophyllum intermediate, the 10-phenyl analogue was substituted for 5-hydroxy-2,2-dimethyl-8-oxo-10-propyl-2H, 8H-pyrano[2,3-f]chromene-6-carbaldehyde (7).

(+)-5-Hydroxy-6-[(1R,2R)-1-tert-butyldimethylsilyloxy-2-methylbut-3-enyl]-2,2-dimethyl-10-propyl-2H-pyrano[2,3-f]chromen-8-one (10)

To a solution of 9 (1.44 g, 3.89 mmol) in dry CH$_2$Cl$_2$ (50 mL) at −20° C. was added pyridine (6 mL), DMAP (1.10 g, 9.00 mmol) and tert-butylchlorodimethylsilane (1.40 g, 9.28 mmol). The reaction mixture was stirred under nitrogen at room temperature for 1.5 h until disappearance of the starting material was observed. Water (15 mL) was then added, and the mixture was stirred for an additional 15 min. The organic layer was separated, and the aqueous layer was extracted with CH$_2$Cl$_2$ (2×15 mL). The combined organic layers were evaporated under reduced pressure at room temperature. The oil obtained was submitted to silica gel chromatography (solvent B) to obtain 10 (1.80 g, 95%) as a syrup: [α]$_D^{20}$+26° (c 3.8, acetone); $^1$H NMR (CDCl$_3$): δ −0.11, 0.08 (2s, 6H, —SiCH$_3$), 0.80 [s, 9H, —C(CH$_3$)$_3$], 0.90 (d, 3H, J=6.90 Hz, —CHCH$_3$), 0.96 (t, 3H, J=7.30 Hz, —CH$_2$CH$_3$), 1.39, 1.43 (2s, 6H, —C(CH$_3$)$_2$), 1.60 (m, 2H, —CH$_2$CH$_3$), 2.54 (m, 1H, —CHCH$_3$), 2.80 (m, 2H, —CH$_2$CH$_2$CH$_3$), 4.86–5.00 (m, 2H, —CH=CH$_2$), 5.22 [d, 1H, J=6.85 Hz, —CHOSi(CH$_3$)$_2$—], 5.46 (d, 1H, J=10.0 Hz, H-3), 5.68–5.87 (m, 1H, —CH=CH$_2$), 5.83 (s, 1H, H-9), 6.59 (d, 1H, J=10.0 Hz, H-4), 9.20 (s, 1H, Ar—OH); $^{13}$C NMR (CDCl$_3$): δ −0.42, −0.22, 13.90, 16.14, 17.95, 23.02, 25.58, 27.47, 27.90, 38.49, 44.45, 74.08, 77.49, 102.63, 106.65, 106.72, 110.00, 115.60, 116.51, 126.61, 139.63, 150.99, 151.69, 155.33, 158.33, 160.90; Anal. Calcd for C$_{28}$H$_{40}$O$_5$Si: C, 69.38; H, 8.32. Found C, 68.55; H, 8.42. MS (negative-ion FAB): m/z 483 (M−1)$^-$, 351, 297.

For preparation of the corresponding inophyllum intermediate, the 10-phenyl analogue was substituted for (+)-5-hydroxy-6-[(1R,2R)-1-hydroxy-2-methylbut-3-enyl], -2,2-dimethyl-10-propyl-2H-pyrano[2,3-f]chromen-8-one (9).

(−)-(10R,11R,12R)-12-tert-Butyldimethylsilyloxy-6,6,10,11-tetramethyl-4-propyl-6,10,11,12-tetrahydrodipyrano[2,3-f;2',3'-h]chromen-2-one (11)

To a solution of 10 (812 mg, 1.68 mmol) in THF (80 mL) was added Hg(OAc)$_2$ (534 mg, 1.68 mmol), and the mixture was stirred for 20 min at room temperature. K$_2$CO$_3$ (232 mg, 1.68 mmol) was then added, and the reaction mixture was stirred for 30 min, then cooled to −10° C. NaBH$_4$ was added (420 g, 11.0 mmol), and the reaction was allowed to warm to room temperature and stir for an additional 15 min. Hexanes (20 mL) were then added, followed by brine (40 mL). The organic layer was separated, and the aqueous layer was extracted with EtOAc (2×25 mL). The combined organic layers were dried (MgSO$_4$), concentrated under reduced pressure at room temperature, and then submitted to silica gel chromatography (solvent B) to give 11 (660 mg, 82%) as a glass: [α]$_D^{20}$ −41° (c 1.0, acetone); $^1$H NMR (CDCl$_3$): δ −0.132, 0.256 (2s, 6H, —SiCH$_3$), 0.792 [s, 9H, —C(CH$_3$)$_3$], 0.996 (t, 3H, J=7.3 Hz, CH$_2$CH$_3$), 1.05 (d, 3H, J=6.82 Hz, —CH$_3$), 1.38 (d, 3H, J=6.35 Hz, —CH$_3$), 1.45, 1.47 (2s, 6H, —C(CH$_3$)$_2$, 1.54–1.73 (m, 3H, H-11,-ch$_2$ch$_3$), 2.87 (m, 2H, —CH$_2$CH$_2$CH$_3$), 4.40 (m, 1H, H-10), 4.99 (d, H, J=2.1 Hz, H-12), 5.49 (d, 1H, J=10.0 Hz, H-7), 5.90 (s, 1H, H-3), 6.62 (d, 1H, J=10.0 Hz, H-8); $_{13}$C NMR (CDCl$_3$): δ −0.91, −0.56, 13.89, 14.05, 18.46, 19.14, 23.10, 25.96, 27.75, 38.49, 39.02, 62.62, 72.91, 77.48, 102.77, 105.83, 106.75, 110.11, 116.63, 126.46, 151.18, 152.92, 153.05, 158.31, 160.54. Anal. Calcd for C$_{28}$H$_{40}$O$_5$Si: C, 69.38; H, 8.32. Found C, 69.18; H, 8.25.

For preparation of the corresponding inophyllum intermediate, the 10-phenyl analogue was substituted for (+)-5-hydroxy-6-[(1R,2R)-1-tert-butyldimethylsilyloxy-2-methylbut-3-enyl]-2,2-dimethyl-10-propyl-2H-pyrano[2,3-f]chromen-8-one (10).

(+)-(10R,11S,12R)-12-Hydroxy-6,6,10,11,-tetramethyl-4-propyl-6,10,11,12-tetrahydrodipyrano[2,3,-f; 2', 3',-h]chromen-2-one (2, calanolide B)

To a solution of 11 (622 mg, 1.28 mmol) in THF (25 mL) was added Bu$_4$NF (12.5 mL, 1 M solution in THF), and the reaction mixture was stirred for 20 min. A mixture of Et$_3$N (65 mg, 0.064 mmol) and HOAc (44 mg, 0.73 mmol) in THF (1.5 mL) was then added, and stirring was continued. The HOAc-Et$_3$N addition was repeated after 2 h, and the reaction was stirred an additional 5 h, after which time the solvent was evaporated. The syrup obtained was then dissolved in EtOAc (30 mL) and washed with water (30 mL). The aqueous layer was separated and extracted with EtOAc (2×30 mL). The combined organic layers were dried (MgSO$_4$) and concentrated. The residue obtained was purified by silica gel chromatography to give 2 (390 mg, 82%) as a white solid: mp 175°–176° C.; [α]$_D^{20}$ +44.0° (c 1.0, acetone); $^1$H NMR (CDCl$_3$): δ 1.00 (t, 3H, J=7.30 Hz, —CH$_2$CH$_3$), 1.10 (d, 3H, J=6.9 Hz, —CH$_3$), 1.40 (d, 3H, J=6.3 Hz, —CH$_3$), 1.45, 1.47 (2s, 6H, —C(CH$_3$)$_2$), 1.62 (m, 2H, —CH$_2$CH$_3$), 1.71 (m, 1H, H-11), 2.86 (m, 2H, H-13), 2.91 (d, 1H, J=3.9 Hz, —OH), 4.24 (m, 1H, H-10), 4.94 (t, 1H, J=3.4 Hz, H-12), 5.50 (d, 1H, J=9.9 Hz, H-7), 5.90 (s, 1H, H-3), 6.61 (d, 1H, J=9.89 Hz, H-8); $^{13}$C NMR (CDCl$_3$): δ 12.46, 13.94, 18.81, 23.20, 27.63, 27.81, 38.26, 38.51, 61.74, 72.94, 77.60, 103.47, 106.08, 106.39, 110.26, 116.55, 126.70, 151.33, 153.12, 153.90, 158.67, 160.95. Anal. Calcd for C$_{22}$H$_{26}$O$_5$: C, 71.33; H, 7.07. Found C, 71.18; H, 7.12.

For preparation of the corresponding inophyllum intermediate, the corresponding 4-phenyl analogue was substituted for (−)-(10R,11R,12R)-12-tert-butyldimethylsilyloxy-6,6,10,11-tetramethyl-4-propyl-6,10,11,12-tetrahydrodipyrano[2,3-f;,2', 3'-h]chromen-2-one (11).

(+)-(10R,11S,12S)-12-Hydroxy-6,6,10,11-tetramethyl-4-propyl-6,10,11,12-tetrahydro-dipyrano[2,3-f;2', 3'-h]chromene-2-one (1, calanolide A)

To a solution of 2 (300 mg, 0.810 mmol) in THF (50 mL) and toluene (50 mL), maintained at −78° C., was added diethyl azodicarboxylate (DEAD, 3.0 mL, 18.92 mmol), PMe$_3$ (18 mL, 1.0 M solution in THF) and chloroacetic acid[21] (1.45 g, 15.3 mmol) in THF (4 mL). The reaction mixture was stirred at −78° C. and allowed to warm up to −30° C. over a period of 1.5 h (until disappearance of starting material was observed by TLC). Ammonium hydroxide (5 mL) was then added, and the solution was concentrated under reduced pressure. The residue obtained was then treated with ammonium hydroxide (14 mL) in MeOH (50 mL), the mixture was stirred for 4.5 h, and then 1:1 EtOAc-hexanes (100 mL) were added. The suspension was stirred for 10 min, filtered, and the filtrate was washed with water (30 mL). The organic layer was separated, dried (MgSO$_4$), concentrated and submitted to silica gel chromatography (solvent A) to give 1 (244 mg, 81%) as a white solid: mp 45°–48° C.; [α]$_D^{20}$+66° (c 0.5, CHCl$_3$); $^1$H NMR (CDCl$_3$): δ 1.03 (t, 3H, J=7.4 Hz, —CH$_2$CH$_3$), 1.14 (d, 3H, J=6.8 Hz, —CH$_3$), 1.46 (d, 3H, J=6.3 Hz, —CH$_3$), 1.46, 1.51 [2s, 6H, —C(CH$_3$)$_2$], 1.66 (m, 2H, —CH$_2$CH$_3$) 1.93 (m, 1H, H-11), 2.89 (m, 2H, —CH$_2$CH$_2$CH$_3$), 3.52 (d, 1H, J=3.0 Hz, —OH), 3.92 (m, 1H, H-10), 4.72 (dd, 1H, J=7.8 Hz, J=2.8 Hz, H-12), 5.54 (d, 1H, J=10.1 Hz, H-7), 5.94 (s, 1H, H-3), 6.62 (d, 1H, J=10.1 Hz, H-8); $^{13}$C NMR (CDCl$_3$): δ 13.96, 15.11, 18.93, 23.24, 27.44, 28.05, 38.64, 40.45, 67.24, 77.20, 77.70, 104.07, 106.38, 106.38 (8a, 12a overlapped), 110.20, 116.55, 126.96, 151.18, 153.11, 154.57, 158.81, 160.32. Anal. Calcd for C$_{22}$H$_{26}$O$_5$·0.2EtOAc: C, 70.57; H, 7.17. Found: C, 70.51; H, 7.20.

For preparation of inophyllum B (3) the 4-phenyl analogue of (+)-calanolide B was substituted for (+)-calanolide B (2).

(−)-5-Hydroxy-6-(1S, 2S)-1-hydroxy-2-methylbut-3-enyl)-2,2-dimethyl-10-propyl-2H-pyrano[2,3-f]chromene-8-one (9a):

The procedure for compound 9 was repeated using (−)-(E)-crotyldiisopinocampheylborane (8a)[5] to give 9a as a syrup: [α]$_D^{20}$ −74° (c 1.0, acetone); $^1$H NMR (CDCl$_3$): δ 0.93 (t, 3H, J=7.40 Hz, —CH$_2$CH$_3$), 0.96 (d, 3H, J=6.80 Hz, —CHCH$_3$), 1.37, 1.42 [2s, 6H, —C(CH$_3$)$_2$], 1.51 (m, 2H, —CH$_2$CH$_3$), 2.55 (m, 1H, —CHCH$_3$), 2.62–2.88 (m, 2H, —CH$_2$CH$_2$CH$_3$), 4.90–5.10 (m, 2H, —CH=CH$_2$), 5.29 (d, 1H, J=7.0 Hz, —CHOH), 5.46 (d, 1H, J=10.0 Hz, H-3), 5.66 (s, 1H, H-9), 5.77–5.96 (m, 1H, —CH=CH$_2$), 6.60 (d, 1H, J=10.0 Hz, H-4), 9.84 (s, 1H, Ar—OH); $^{13}$C NMR (CDCl$_3$): δ 13.98, 16.42, 28.08, 38.51, 44.24, 72.57, 77.61, 102.78, 106.21, 23.01, 27.42, 107.11, 109.23, 116.56 (C-4, CH=CH$_2$ overlapped), 126.73, 139.68, 151.09, 151.81, 155.95, 159.33, 161.56. Anal. Calcd for C$_{22}$H$_{26}$O$_5$: C, 71.33; H, 7.07. Found: C, 71.33; H, 7.13.

For preparation of the corresponding inophyllum intermediate, the 10-phenyl analogue of 5-hydroxy-2,2-dimethyl-8-oxo-10-propyl-2H,8H-Pyrano[2,3-f]chromene-6-carbaldehyde (7) was used.

(−)-5-Hydroxy-6-[(1S,2S)-tert-butyldimethylsilyloxy-2-methylbut-3-enyl]-2,2-dimethyl-10-pyropyl-2H-pyrano[2,3-f]chromen-8-one (10a)

By the same procedure as for compound 10, 10a was obtained as a syrup: [α]$_D^{20}$ −23° (c 3.8, acetone); $^1$H NMR (CDCl$_3$): −0.11, 0.08 (2s, 6H, —SiCH$_3$), 0.80 [s, 9H, —C(CH$_3$)$_3$], 0.90 (d, 3H, J=6.90 Hz, —CHCH$_3$), 0.96 (t, 3H, J=7.30 Hz, —CH$_2$CH$_3$), 1.39, 1.43 [2s, 6H, —C(CH$_3$)$_2$], 1.60 (m, 2H, —CH$_2$CH$_3$), 2.54 (m, 1H, —CHCH$_3$), 2.80 (m, 2H, —CH$_2$CH$_2$CH$_3$), 4.86–5.00 (m, 2H, —CH=CH$_2$), 5.22 (d, 1H, J=6.85 Hz, —CHOSi(CH$_3$)$_2$—), 5.46 (d, 1H, J=10.0 Hz, H-3), 5.68–5.87 (m, 1H, —CH=CH$_2$), 5.83 (s, 1H, H-9), 6.59 (d, 1H, J=10.0 H$_z$, H-4), 9.21 (s, 1H, At—OH); $^{13}$C NMR (CDCl$_3$): δ −0.40, −0.20, 13.90, 16.13, 17.93, 23.02, 25.57, 27.45, 27.88, 38.49, 44.44, 74.07, 77.48, 102.62, 106.63, 106.71, 110.00, 115.58, 116.51, 126.58, 139.62, 150.99, 151.69, 155.33, 158.29, 160.36; Anal. Calcd for $C_{28}H_{40}O_5Si$: C, 69.38; H, 8.32. Found: C, 68.56; H, 8.32; MS (negative-ion FAB): m/z 483 (M−1)⁻, 351, 297.

For preparation of the corresponding inophyllum intermediate, the 10-phenyl analogue of (−)-5-hydroxy-6-[(1S, 2S)-1-hydroxy-2-methylbut-3-enyl]-2,2-dimethyl-10-propyl-2H-pyrano[2,3-f]chromen-8-one (9A) was used.

(+)-(10S,11S,12S)-tert-Butyldimethylsilyloxy-6,6,11,12-tetramethyl-4-propyl-6,10,11,12-tetrahydrodipyrano[2,3-f;2', 3'-h]chromen-2-one (11a):

By the procedure used for compound 11, 11 a was obtained as a syrup: $[\alpha]_D^{20}$ +41.5° (c 1.0, acetone); ¹H NMR (CDCl₃): δ −0.11, 0.28 (2s, 6H, —SiCH₃), 0.82 [s, 9H, —C(CH₃)₃], 1.02 (t, 3H, J=7.3 Hz, —CH₂CH₃), 1.08 (d, 3H, J=6.8 Hz, —CH₃), 1.40 (d, 3H, J=6.35 Hz, —CH₃), 1.48, 1.50 [2s, 6H, —C(CH₃)₂], 1.56–1.74 (m, 3H, H-11, —CH₂CH₃), 2.89 (m, 2H, —CH₂CH₂CH₃), 4.42 (m, 1H, H-10), 5.01 (d, H, J=2.1 Hz, H-12), 5.52 (d, 1H, J=10.0 Hz, 5.01 (d, H, J=2.1 Hz, H-12), H-7), 5.92 (s, 1H, H-3), 6.64 (d, 1H, J=10.0 Hz, H-8); ¹³C NMR (CDCl₃): δ −0.85, −0.51, 13.93, 14.10, 18.53, 19.20, 23.15, 26.02, 27.81, 38.55, 39.09, 62.69, 73.0, 77.52, 102.85, 105.90, 106.84, 110.18, 116.70, 126.53, 151.24, 152.98, 153.12, 158.39, 160.64. Anal. Calcd for $C_{28}H_{40}O_5Si$: C, 69.38; H, 8.32. Found C, 69.14; H, 8.36.

For preparation of the corresponding inophyllum intermediate, the 10-phenyl analogue of (−)-5-hydroxy-6-[(1S, 2S)-1-tert-butyldimethylsilyoxy-2-methylbut-3-enyl]-2,2-dimethyl-10-propyl-2H-pyrano[2,3-f]chromen-8-one (10) was used.

(−)-(10S,11R,12S)-12-Hydroxy-6,6,10,11-tetramethyl-4-propyl-6,10,11,12-tetrahydro-dipyrano[2,3-f;2',3'-h] chromen-2-one (2a, costatolide⁷ᵃ or (−)-calanolide B)

By the procedure used for compound 2, 2a was obtained as a white solid: mp 176°–177° C.; $[\alpha]_D^{20}$ −45.0° (c, 1.0, acetone); ¹H NMR (CDCl₃): δ 1.03 (t, 3H, J=7.30 Hz, —CH₂CH₃), 1.14 (d, 3H, J=6.9 Hz, —CH₃), 1.43 (d, 3H, J=6.3 Hz, —CH₃), 1.48, 1.49 [2s, 6H, —C(CH₃)₂], 1.65 (m, 2H, —CH₂CH₃), 1.74 (m, 1H, H-11), 2.59 (d, 1H, J=3.7 Hz, —OH), 2.89 (m, 2H, H-13), 4.26 (m, 1H, H-10), 4.97 (t, 1H, J=3.4 Hz, H-12), 5.53 (d, 1H, J=9.9 Hz, H-7), 5.94 (s, 1H, H-3), 6.63 (d, 1H, J=9.89 Hz, H-8); ¹³C NMR (CDCl₃): δ 12.46, 13.94, 18.81, 23.20, 27.63, 27.81, 38.26, 38.51, 61.75, 72.94, 77.60, 103.47, 106.06, 106.37, 110.27, 26 68, 151.33, 153.12, 153.90, 158.63, 160.91. Anal. Calcd for $C_{22}H_{26}O_5$: C, 71.33; H, 7.07. Found: C, 71.41; H, 7.16.

For preparation of the inophyllum analogue of (−)-calanolide B, the 4-phenyl analogue of (+)-(10S,11S,12S)-12-tert-butyldimethylsilyloxy-6,6,10,11-tetramethyl-4-propyl-6,10,11,12-tetrahydrodipyrano[2,3-f;2',3'-h]chromen-2-one (11a) was used.

(−)-(10S,11R,12R)-12-Hydroxy-6,6,10,11-tetramethyl-4-propyl-6,10,11,12-tetrahydro-dipyrano[2,3-f;2',3'-h] chromene-2-one (1a, (−)-calanolide A)

By the procedure for compound 1, compound 1a was obtained as a white solid: mp 44°–47° C.; $[\alpha]_D^{20}$ −66° (c 0.5, CHCl₃); ¹H NMR (CDCl₃): δ 1.03 (t, 3H, J=7.4 Hz, —CH₂CH₃), 1.14 (d, 3H, J=6.8 Hz, —CH₃), 1.46 (d, 3H, J=6.3 Hz, —CH₃), 1.46, 1.51 [2s, 6H, —C(CH₃)₂], 1.66 (m, 2H, —CH₂CH₃), 1.93 (m, 1H, H-11), 2.89 m, 2H, —CH₂CH₂CH₃), 3.49 (d, 1H, J=2.5 Hz, —OH), 3.92 (m, 1H, H-10), 4.72 (dd, 1H, J=7.8 Hz, J=2.8 Hz, H-12), 5.54 (d, 1H, J=10.1 Hz, H-7), 5.94 (s, 1H, H-3), 6.62 (d, 1H, J=10.1 Hz, H-8); ¹³C NMR (CDCl₃): δ 13.96, 15.11, 18.93, 23.24, 27.45, 28.05, 38.65, 40.46, 67.25, 77.19, 77.70, 104.07, 106.38, 106.38 (8a, 12a overlapped), 110.20, 116.55, 126.97, 151.18, 153.12, 154.57, 158.82, 160.34. Anal. Calcd for $C_{22}H_{26}O_5$: C, 71.33; H, 7.07. Found: C, 71.30; H, 7.11.

For preparation of the inophyllum analogue of (−)-calanolide A, the 4-phenyl analogue of (−)-calanolide B (2a) was used.

The antiviral properties of the compounds obtained in accordance with the method of the invention are illustrated hereinafter.

The anti-HIV drug testing protocol is that of Weislow, O. W., Kiser, R., Fine, D., Bader, J., Shoemaker, R. H., Boyd, M. R., "New soluble-formazan assay for HIV-1 cytopathic effects; application to high-flux screening of synthetic and natural products for AIDS-antiviral activity", *J. Natl. Cancer Inst.*, 81:577–586, 1989. The procedure is used in the National Cancer Institute's test for agents active against human immunodeficiency virus (HIV) is designed to detect agents acting at any stage of the virus reproductive cycle. The assay basically involves the killing of T4 lymphocytes by HIV. Small amounts of HIV are added to cells, and two cycles of virus reproduction are necessary to obtain the required cell killing. Agents that interact with virions, cells, or virus gene-products to interfere with viral activities will protect cells from cytolysis. The system is automated in several features to accommodate large numbers of candidate agents and is generally designed to detect anti-HIV activity. However, compounds that degenerate or are rapidly metabolized in the culture conditions may not show activity in this screen.

The Procedure:

1. Candidate agent is dissolved in dimethyl sulfoxide (unless otherwise instructed) then diluted 1:100 in cell culture medium before preparing serial half $\log_{10}$ dilutions. T4 lymphocytes (CEM cell line) are added and after a brief interval HIV-1 is added, resulting in a 1:200 final dilution of the compound. Uninfected cells with the compound serve as a toxicity control and infected and uninfected cells without the compound serve as basic controls.

2. Cultures are incubated at 37° C. in a 5% carbon dioxide atmosphere for 6 days.

3. The tetrazolium salt, XTT, is added to all wells and cultures are incubated to allow formazan color development by viable cells.

4. Individual wells are analyzed spectrophotometrically to quantitate formazan production, and in addition are viewed microscopically for detection of viable cells and confirmation of protective activity.

5. Drug-treated virus-infected cells are compared with drug-treated non-infected cells and with other appropriate controls (untreated infected and untreated non-infected cells, drug-containing wells without cells, etc.) on the same plate.

6. Data are reviewed in comparison with other tests done at the same time and a determination about activity is made.

The results of anti-HIV-1 activities of the calanolides tested are shown in Table 1 from which it can be seen that two of the calanolides are highly potent anti-HIV-1 compounds; the other two have milder activity.

When the inophyllums are synthesized by the method of the invention, it is expected that they will likewise show comparable anti-HIV-1 activity.

TABLE I

Anti-HIV Screening

| Name | IC$_{50}$ (M) | EC$_{50}$ (M) | TI |
|---|---|---|---|
| (−)-Calanolide A | $3.23 \times 10^{-6}$ | $3.04 \times 10^{-7}$ | 10.6 |
|  | $3.27 \times 10^{-6}$ | $3.46 \times 10^{-7}$ | 9.45 |
| (+)-Calanolide B | $3.92 \times 10^{-6}$ | $1.47 \times 10^{-6}$ | 2.68 |
|  | $3.50 \times 10^{-6}$ | $5.63 \times 10^{-6}$ | 6.21 |
| (+)-Calanolide A | $>2.0 \times 10^{-6}$ | $3.52 \times 10^{-8}$ | >56.8 |
|  | $>2.0 \times 10^{-6}$ | $5.87 \times 10^{-9}$ | >340 |
| (−)-Calanolide B | $>2.0 \times 10^{-6}$ | $2.03 \times 10^{-8}$ | >98.6 |
| (costatolide) | $>2.0 \times 10^{-6}$ | $4.83 \times 10^{-9}$ | >414 |

IC$_{50}$ = is the 50% inhibitory concentration for cell growth.
EC$_{50}$ = is the 50% effective concentration against HIV cytopathic effects.
TI = Therapeutic Index, which is IC$_{50}$/EC$_{50}$.

The antiviral compounds produced in accordance with the invention are useful to inhibit the growth or replication of a virus, specifically a human immunodeficiency virus, such as HIV-1 or HIV-2. Biological compositions comprising the compounds synthesized by the method of the invention as described in various publications such as the PCT publications which are referred to above and incorporated by reference.

As one skilled in the art will appreciate, the antiviral compounds probably will inhibit other retroviruses and may inhibit viruses, other than retroviruses. Examples of viruses that may be treated in accordance with the present invention include, but are not limited to, Type C and Type D retroviruses, HTLV-1, HTLV-2, HIV, FLV, SIV, MLV, BLV, BIV, equine infectious, anemia virus, avian sarcoma viruses, such as rous sarcoma virus (RSV), hepatitis type A, B, non-A, and non-B viruses, herpes viruses, cytomegaloviruses, influenza viruses, arboviruses, varicella viruses, measles, mumps and rubella viruses, as disclosed in PCT publication WO 94/2800.

The compounds synthesized by the invention can be administered with other anti-retroviral agents, particularly with known reverse transcriptase inhibitors such as ddC, AZT, ddI, ddA, and other inhibitors that act against other HIV proteins, such as anti-TAT agents, and will generally inhibit most or all replicative stages of the viral life cycle. See PCT publication WO 94/28000, which is incorporated herein by reference.

The compositions comprising calanolides and related compounds and derivatives thereof have been disclosed to treat a virally infected animal, such as a human. Such compositions also have been noted to find utility in the prophylactic treatment when the subject is at risk for viral infection. See, PCT publication WO 94/28000.

WO 94/14789 provides a detailed description of various inophyllums, calanolides and other coumarin derivatives The dosages suggested for administration have been also published in the said PCT publications.

The above examples and description fully disclose the present invention including preferred embodiments thereof. The invention however, is not limited to the precise embodiments described herein but includes all modifications encompassed with the scope and spirit of the following claims.

References, Patents and Footnotes 1. (a) Kashman, Y.; Gustafson, K. R.; Fuller, R. W.; Cardellina, J. H., II; McMahon, J. B.; Currens, M. J.; Buckhiet, R. W., Jr.; Hughes, S. H.; Cragg, G. M.; Boyd, M. R. *J. Med. Chem.* 1992, 35, 2735–2743. (b) Fuller, R. W.; Bokesh, H. R.; Gustafson, K. R.; McKee, T. C.; Cardelina II, J. H.; McMahon, J. B.; Cragg, G. M.; Soejarto, D. D.; Boyd, M. R. *Bioorg. Med. Chem. Lett.* 1994, 4, 1961–1964. (c) Newman, R. A.; Costa, M.; Cisneros, A. *J. Chromatogr. B* 1994, 658, 129–133.
2. (a) Kawazu, K.; Ohigashi H.; Mitsui, T. *Tetrahedron Lett.* 1968, 2383–2385. (b) Kawazu, K.; Ohigashi H.; Takahashi, N.; Mitsui, T. *Bull. Chem. Res. Kyoto Univ.* 1972, 50, 160–167; *Chem. Abstr.* 78:13744.
3. Patil, A. D.; Freyer, A. J.; Eggleston, D. S.; Haltiwagner, R. C.; Bean, M. F.; Taylor, P. B.; Caranfa, M. J.; Breen, A. L.; Bartus, H. R.; Johnson, R. K.; Hertzberg, R. P.; Westly, J. W. *J. Med. Chem.* 1993, 36, 4130–4138.
4. Taylor, P. B.; Culp, J. S.; Debouck, C.; Johnson, R. K.; Patil, A. D.; Woolf, D. J.; Brooks, I.; Hertzberg, R. P. *J. Biol. Chem.* 1994, 269, 6325–6331.
5. Chenera, B.; West, M. L.; Finkelstein, J. A.; Dreyer, G. B. *J. Org. Chem.* 1993, 58, 5605–5606.
6. Palmer, C. J.; Josephs, J. L. *Tetrahedron Lett.* 1994, 35, 5363–5366.
7. (a) Stout, G. H.; Stevens, K. L. *J. Org. Chem.* 1964, 29, 3604–3609; (b) Stout, G. H.; Hickernell, G. K.; Sears, K. D. *J. Org. Chem.* 1968, 33, 4191–4200.
8. Polonsky, J. *Bull. Soc. Chim. Ft.* 1956, 914–922; Polonsky, J.; Baskevitch, Z. *Bull. Soc. Chim. Ft.* 1958, 929–944.
9. Rao, A. V. R.; Gaitonde, A. S.; Prakash, K. R. C.; Rao, S. P. *Tetrahedron Lett.* 1994, 35, 6347–6350.
10. Deshpande, P. P.; Baker D. C. *Synthesis,* in press.
11. (+)-Calanolide A[1a] and (−)-calanolide B (known as costatolide)$^{TM}$ are firmly established natural products. Recently[1a] (+)-calanolide B has been reported as a natural product; however, subsequent studies to those reported[1a] have indicated that the product was impure. (Details are to be published.) Thus the $[\alpha]_D+10°$ (c 1.0, acetone)[1a] is in
12. Murray, R. D. H.; Mendez, J.; Brown, S. A. *The Natural Coumarins,* Wiley: Bristol, 1982, pp 55–95
13. Vilsmeier, J. C. *Adv. Org. Chem.* 1976, 9, 225–342.
14. Reference 12, pp 131–161
15. Brown, H. C.; Bhat, K. S. *J. Am. Chem. Soc.* 1986, 108, 5919–5923
16. Tius, M. A.; Busch-Petersen, J. *Tetrahedron Lett.* 1994, 35, 5181–5184.
17. Kabalka, G. W.; Shoup, T. M.; Goudgaon, N. M. *J. Org. Chem.* 1989, 54, 5930–5933.
18. Clive, D. L. J.; Chittattu, G.; Curtis, N. J.; Kiel, W. A.; Wong, C. K. J. C. *S. Chem. Soc., Chem. Commun.* 1977, 725–727.
19. Brown, H. C.; Rei, M. -H. *J. Am. Chem. Soc.* 1969, 91, 5646–5649.
20. Dale, J. A.; Dull, D. L.; Mosher, H. S. *J. Org. Chem.* 1969, 34, 2543–2549
21. Sarah, M.; Bessodes, M.; Antonakis, K. *Tetrahedron Lett.* 1992, 33, 4317–4320.
22. Mitsunobu, O. *Synthesis,* 1981, 1–28.
23. Schaumberg, J. P.; Hokanson, G. C.; French, J. C.; Smal, E.; Baker, D. C. *J. Org. Chem.* 1985, 50, 1651–1656, footnote 33 therein
24. Brown, H. C.; Jadhav, P. K.; Mandal, A. K., *J. Org. Chem.,* 1982, 47, 5074.
25. Jadhav, P. K.; Kulkarni, J., *Heterocycles,* 1982, 18, 169.
26. Brown, H. C.; Vara Prasad, J. V. N., Zaidlewicz, M., *J. Org. Chem,* 1988, 53, 2911.
27. de Richter, R. K.; Bonato, M.; Follet, M.; Kamenka, J. M., *J. Org. Chem.,* 1990, 55, 2855.
28. Jadhav, P. K.; Brown, H. C., *J. Org. Chem.,* 1981, 46, 2988.
29. PCT International Publication WO 93/2008, published Oct. 14, 1993, Boyd, et al., Calanolide Antiviral Compounds, Compositions and Uses Thereof.

30. PCT International Publication WO 94/14789, published Jul. 7, 1994, Patil, et al., Coumarin Derivatives as Retroviral Inhibitors.

31. PCT International Publication WO 94/28000, published Dec. 8, 1994, Boyd, et al., Calanolide and Related Antiviral Compounds, Compositions, and Uses Thereof.

We claim:

1. A method for the synthesis of optically active (+)-calanolide B which comprises the steps of
   (a) ring formylation at the C-8 position of coumarin lactone (5), thereby obtaining the C-8 formylated derivative (6),
   (b) causing chromene ring formation by reacting and heating in an organic solvent the mixture of the formylated derivative (6) with a propargylic halide, in the presence of a base and Bu$_4$NI, followed by the addition of a Lewis acid, thereby obtaining the chromene-6-carbaldehyde (7),
   (c) forming the enantiomerically pure trans-2,3-dimethyl chroman-4-ol by hydroboration of said aldehyde with (+)-optically active (+)-(E)-crotyldiisopinocampheylborane at a temperature of about −93° to about −78° C.,
   (d) oxidizing the boron-carbon bond, thereby obtaining threo-β-methylhomoallylic alcohol (9),
   (e) monosilylating said secondary alcohol, thereby obtaining the monosilylated orthoalkenyl phenol (10),
   (f) causing Hg-mediated ring closure of (10),
   (g) reducing the organomercurial intermediate, thereby obtaining the silyl-protected calanolide B derivative (11),
   (h) removing the silyl group, thereby obtaining pure (+)-calanolide B, free by at least 95% of its enantiomer, and
   (i) isolating said (+)-calanolide B.

2. A method of synthesis of the optically and biologically active (+)-calanolide A which comprises esterifying and inverting the C-12 OH group of (+)-calanolide B with the combination of PMe$_3$, diethylazodicarboxylate and chloroacetic acid, saponifying the resulting ester, and isolating and purifying the (+)-calanolide A free by at least 95% of its enantiomer.

3. A method of synthesis of the optically and biologically active (−)-calanolide B which comprises the steps of
   (a) ring formylation at the C-8 position of coumarin lactone (5), thereby obtaining the C-8 formylated derivative (6),
   (b) causing chromene ring formation by reacting and heating in an organic solvent the mixture of the formylated derivative (6) with a propargylic halide, in the presence of a base and Bu$_4$NI, followed by the addition of a Lewis acid, thereby obtaining the chromene-6-carbaldehyde (7),
   (c) forming the enantiomerically pure trans-2,3-dimethyl chroman-4-ol by hydroboration of said aldehyde with (−)-optically active (−)-(E)-crgtyldiisopinocampheylborane at a temperature of about −93° to about −78° C.,
   (d) oxidizing the boron-carbon bond, thereby obtaining the (−)-threo-homoallylic alcohol (9a),
   (e) monosilylating said secondary alcohol, thereby obtaining the monosilylated orthoalkenyl phenol (10a),
   (f) causing Hg-mediated ring closure of (10a),
   (g) reducing the organomercurial intermediate, thereby obtaining the silyl-protected calanolide B derivative (11a),
   (h) removing the silyl group, thereby obtaining pure (−)-calanolide B, free by at least 95% of its enantiomer, and
   (i) isolating said (−)-calanolide B (2a).

4. A method of synthesis of the optically active (−)-calanolide A which comprises esterifying (−)-calanolide B with PMe$_3$, diethylazodicarboxylate and chloroacetic acid, saponifying the resulting ester and isolating the (−)-calanolide A free by at least 95% of its enantiomer.

5. The method of claim 1 wherein the isolated (+)-calanolide B is pure and has an optical rotation of $[\alpha]_D^{20}=+44°$ (c 1, CH$_3$COCH$_3$).

6. The method of claim 2 wherein the isolated (+)-calanolide A is pure, containing only about 2% of its optical isomer (−)-calanolide A, has an optical rotation of $[\alpha]_D^{20}=+66°$ (c 0.5, CHCl$_3$) and has anti-HIV-1 activity (measured by the Weislow, et al. formazan test).

7. The method of claim 3 wherein the isolated (−)-calanolide B is pure, containing only about 2% of its optical isomer (+)-calanolide B, has an optical rotation of $[\alpha]_D^{20}=-45°$ (c 1, CH$_3$COCH$_3$) and has anti-HIV-1 activity (measured by the Weislow, et al. formazan test).

8. The method of claim 4 wherein the isolated (−)-calanolide A is pure and has an optical rotation of $[\alpha]_D^{20}=-66°$ (c 0.5, CHCl$_3$).

9. The process of claim 5 wherein the isolated (+)-calanolide B has a melting point of 175°–176° C.

10. The process of claim 6 wherein the isolated (+)-calanolide A has a melting point of 45°–48° C.

11. The process of claim 7 wherein the isolated (−)-calanolide B has a melting point of 176°–177° C.

12. The process of claim 8 wherein the isolated (−)-calanolide A has a melting point of 44°–47° C.

13. A method for the synthesis of optically active (+)-calanolide B which comprises the steps of
   (a) ring formylation at C-8 of compound (5), thereby obtaining the C-8 formylated derivative (6),
   (b) reacting said aldehyde with a (+)-optically active (+)-(E)-crotyldiisopinocampheylborane at a temperature of about −93° to about −78° C., thereby obtaining the alcohol (4) (shown in Scheme 3),
   (c) monosilylating of secondary alcohol (14) to give the protected derivative (15),
   (d) causing chromene ring formation by reacting and heating in an organic solvent the mixture of the protected secondary alcohol (15) with a propargylic halide, in the presence of a base and Bu$_4$NI, followed by the addition of a Lewis acid, thereby obtaining the compound (10) (shown in Scheme 3), and thereafter carrying out steps f through i of claim 1.

14. The method of claim 1 which comprises isolating the crystalline formylated lactone (6).

15. The method of claim 1 which comprises isolating the solid chromene-6-carbaldehyde (7).

16. The method of claim 1 which comprises isolating the threo-β-methylhomoallylic alcohol (9).

17. The method of claim 1 which comprises isolating the silyl-protected calanolide B derivative (11).

18. The method of claim 3 which comprises isolating the silyl protected calanolide B derivative (11a).

19. The method of claim 1 which comprises isolating the monosilylated orthoalkenyl phenol (10).

20. The method of claim 3 which comprises isolating the (−)-threo-homoallylic alcohol (9a).

21. The method of claim 3 which comprises isolating the monosilylated orthoalkenyl phenol (10a).

* * * * *